US009018452B2

(12) United States Patent
Collin et al.

(10) Patent No.: US 9,018,452 B2
(45) Date of Patent: Apr. 28, 2015

(54) HYBRID MELON VARIETY 34-765 RZ

(71) Applicant: Rijk Zwaan Zaadteelt en Zaadhandel B.V., De Lier (NL)

(72) Inventors: Laurence Catherine Collin, Villeneuve-lez-Avignon (FR); Albertus Cornelius Maria van den Ende, De Lier (NL)

(73) Assignee: Rijk Zwaan Zaadteelt en Zaadhandel B.V., De Lier (NL)

(*) Notice: Subject to any disclaimer, the term of this patent is extended or adjusted under 35 U.S.C. 154(b) by 0 days.

(21) Appl. No.: 13/798,953

(22) Filed: Mar. 13, 2013

(65) Prior Publication Data

US 2014/0283189 A1 Sep. 18, 2014

(51) Int. Cl.

| | |
|---|---|
| ***A01H 5/10*** | (2006.01) |
| ***A01H 5/00*** | (2006.01) |
| ***A01H 4/00*** | (2006.01) |
| ***A01H 5/08*** | (2006.01) |
| ***C12N 15/82*** | (2006.01) |
| ***C12Q 1/68*** | (2006.01) |

(52) U.S. Cl.
CPC .............. *A01H 5/08* (2013.01); *C12N 15/8241* (2013.01); *C12Q 1/6895* (2013.01)

(58) Field of Classification Search
None
See application file for complete search history.

(56) References Cited

U.S. PATENT DOCUMENTS 6,160,208 A * 12/2000 Lundquist et al. ......... 800/320.1

* cited by examiner

*Primary Examiner* — Brent T Page
(74) *Attorney, Agent, or Firm* — Vedder Price P.C.; Thomas J. Kowalski; Deborah L. Lu

(57) ABSTRACT

The present invention relates to a *Cucumis melo* seed designated 34-765 RZ, which may exhibit a medium to dark greyish green color of the young fruit, a circular fruit shape in longitudinal section, a green ground color of the fruit skin with medium intensity and a yellowish hue, a small to medium size of the pistil scar, a reddish orange flesh color, and intermediate resistance to powdery mildew *Podosphaera xanthii* (Px) race 1, race 2, race 5. The present invention also relates to a *Cucumis melo* plant produced by growing the 34-765 RZ seed. The invention further relates to methods for producing the melon cultivar, represented by melon variety 34-765 RZ.

36 Claims, No Drawings

HYBRID MELON VARIETY 34-765 RZ

INCORPORATION BY REFERENCE

All documents cited or referenced herein ("herein cited documents"), and all documents cited or referenced in herein cited documents, together with any manufacturer's instructions, descriptions, product specifications, and product sheets for any products mentioned herein or in any document incorporated herein by reference, are hereby incorporated herein by reference, and may be employed in the practice of the invention.

FIELD OF THE INVENTION

The present invention relates to a new hybrid melon (*Cucumis melo*) variety 34-765 RZ which exhibits a combination of traits such as a medium to dark greyish green color of the young fruit, a circular fruit shape in longitudinal section, a green ground color of the fruit skin with medium intensity and a yellowish hue, a small to medium size of the pistil scar, a reddish orange flesh color, and intermediate resistance to powdery mildew *Podosphaera xanthii* (Px) race 1, race 2, race 5.

BACKGROUND OF THE INVENTION

Melon plants of the species *Cucumis melo* belong to the cucurbit family, scientifically called the Cucurbitaceae. Within this family it belongs to the genus *Cucumis*, which does not only harbor a variety of melon types, but also the important food crop cucumber, *Cucumis sativus*, as well as several other, less well-known species. It is an annual, herbaceous, flowering plant species which appears to have originated in Africa or possibly Asia.

The species *Cucumis melo* has taxonomically been classified in various ways over the years, for example using a division into subspecies *melo* and *agrestis* with further classification into varieties, wherein basically all cultivated melons belong to the ssp. *melo*.

Another classification divides *C. melo* into 7 taxonomic varieties, one of which combines all wild types (*C. melo* var. *agrestis*), and the other six include the cultivated melons. These six cultivated varieties are *cantalupensis, inodorus, flexuosus, conomon, dudaim*, and *momordica*. The cultivated netted melon types muskmelon and cantaloupe, which include for example Galia, Charentais, Ogen, and Eastern and Western shippers, in this classification belong to *C. melo* var. *cantalupensis*. The other main group of sweet melons, such as Honeydews, and Cassaba types (e.g. Piel de Sapo, Jaune Canari) belong to *C. melo* var. *inodorus*, which harbours non-climacteric and generally less or non-aromatic melon types with a better shelf life than *cantalupensis*.

Most non-sweet melons are grouped into the other taxonomic varieties, including for example snake melon, which is eaten immature as an alternative for cucumber, and belongs to *C. melo* var. *flexuosus*.

Melon plants were domesticated early and have been cultivated for thousands of years in African and Asian countries. They are presently cultivated worldwide for their delicious and highly nutritious fruits, and are a good source of vitamin C and potassium. Depending on the type they can also provide useful amounts of other compounds such as vitamin A, B6, and folate. Melons are typically consumed fresh, in salads or prepared into desserts, appetizers, or drinks, for which they can be combined with a variety of other ingredients.

In 2011, the total acreage for cantaloupes in the United States was approximately 70,950 acres, with a total production of about 18.8 million cwt, representing a value of just over $349.7 million. Honeydews were harvested from 14,400 acres which resulted in a production of about 3.2 million cwt, having a value of approximately $70.7 million (source: USDA/NASS 2012).

Melon production is most successful in a climate with a long warm sunny season that is relatively dry. Several pests and diseases can affect melon production, including several viruses that are often transferred by insects, but also nematodes, bacterial and fungal diseases. Typical problems that might arise during melon production include *Fusarium oxysporum* f. sp. *melonis* (Fom) race 0, race 1, race 2, or race 1, 2; downy mildew (*Pseudoperonospora cubensis*); powdery mildew (*Podosphaera xanthii* or *Golovinomyces cichoracearum*); gummy stem blight (*Didymella bryoniae*); sudden wilt, including infection by *Monosporascus cannonballus; Alternaria cucumerina*; bacterial wilt (*Erwinia tracheiphila*); the viruses Melon Necrotic Spot Virus (MNSV), Watermelon Mosaic Virus (WMV), Cucurbit Yellow Stunting Disorder Virus (CYSDV), Cucumber Vein Yellowing Virus (CVYV), Cucumber Mosaic Virus (CMV), Papaya Ringspot Virus (PRSV), Zucchini Yellow Mosaic Virus (ZYMV); and insect attacks by cotton aphids (*Aphis gossypii*), pickleworm, whitefly (*Bemisia tabaci*), and leafminer.

Breeding for resistance against any of the diseases and pests that are mentioned above, or any other biotic or abiotec stress factors, is an important aspect in providing varieties for multiple growing systems and climates. It is preferred to breed for a combination of resistances to create a variety that is most suitable in a certain situation or environment.

In order to create melon varieties that are satisfying the needs of growers and/or consumers, many considerations have to be taken into account. The goal in a breeding programme is to combine within a single variety or hybrid an improved combination of desirable traits from the parental germplasms. These traits may include higher yield, field performance, resistance to diseases and insects, and tolerance to drought and heat. For melons it is apparent that fruit quality is of the utmost importance, which includes aspects such as external and internal color, content in soluble solids including sweetness, aroma, texture, juiciness, size of the seed cavity, firmness, and shelf life. In addition, characteristics related to optimum plant development are very important for the grower, such as uniformity and speed of germination, growth rate, time to maturity, and plant uniformity.

Melon is a diploid plant species with twelve pairs of chromosomes. Cultivated melon plants can have different flower types, which can be present in various combinations. The situations that are most common are monoecious plants, containing male and female flowers, and andromonoecious plants, which combine male and hermaphrodite flowers. Other sex expressions that are occurring in melon are gynoecious and hermaphrodite; in these cases only female or hermaphrodite flowers are present respectively. The sex expression of melon is extensively studied, and two genes involved in determining the type and combination of flowers in a melon plant have been identified.

Melon plants in principle are self-pollinators but cross pollination occurs frequently, predictably also depending on the type of flowers that is present. The presence of pollinating insects facilitates both self- and cross-pollination. Like in most crops, commercial melon cultivars were initially open-pollinated, but nowadays many high yielding hybrid varieties are available. Melons are grown throughout the world, in open field as well as protected cultivation, and are adapted to many different climates and circumstances. As mentioned earlier, many different types are available, and different regions have different preferences in type, size, flesh color, taste, etc. Since all melon types belong to the same species, no crossing barriers exist and combinations between types are frequently developed in breeding programmes, although some specific type characteristics might be difficult to recombine into a new type.

The habit of a melon plant contributes to the overall performance and ultimately to the development and yield of the melon fruits. A strong plant with a good vigor is a good starting point for well developing fruits in reaching a high yield. A fruit color and type that is suited to and attractive for the intended consumers plays an important role in the success of a variety. An attractive and recognizable external appearance and an appealing flesh color are strong marketing tools. The ability to recognize whether fruits are getting overmature is a useful aspect of fruit quality.

Growers rely on the presence of resistances to pests and diseases in anticipation of a good melon crop. In addition, the presence of resistances requires lower pesticide inputs, which benefits both the costs for the farmer and the environment. A pistil scar that is not large reduces the chances of infection by diseases.

Citation or identification of any document in this application is not an admission that such document is available as prior art to the present invention.

SUMMARY OF THE INVENTION

There exists a need for a hybrid melon variety which exhibits a combination of traits such as a medium to dark greyish green color of the young fruit, a circular fruit shape in longitudinal section, a green ground color of the fruit skin with medium intensity and a yellowish hue, a small to medium size of the pistil scar, a reddish orange flesh color, and intermediate resistance to powdery mildew *Podosphaera xanthii* (Px) race 1, race 2, race 5.

The present invention fulfills this need by providing a new melon (*Cucumis melo*) variety, designated 34-765 RZ. Melon cultivar 34-765 RZ exhibits a combination of traits such as a medium to dark greyish green color of the young fruit, a circular fruit shape in longitudinal section, a green ground color of the fruit skin with medium intensity and a yellowish hue, a small to medium size of the pistil scar, a reddish orange flesh color, and intermediate resistance to powdery mildew *Podosphaera xanthii* (Px) race 1, race 2, race 5.

The present invention provides seeds of melon cultivar 34-765 RZ, which have been deposited with the National Collections of Industrial, Marine and Food Bacteria (NCIMB) in Bucksburn, Aberdeen AB21 9YA, Scotland, UK and have been assigned NCIMB Accession No. 42128.

In one embodiment, the invention provides a melon plant which may exhibit a combination of traits including a medium to dark greyish green color of the young fruit, a circular fruit shape in longitudinal section, a green ground color of the fruit skin with medium intensity and a yellowish hue, a small to medium size of the pistil scar, a reddish orange flesh color, and intermediate resistance to powdery mildew *Podosphaera xanthii* (Px) race 1, race 2, race 5, representative seed of which have been deposited under NCIMB Accession No. 42128.

In one embodiment, the invention provides a melon plant which may exhibit a combination of traits including a medium to dark greyish green color of the young fruit, a circular fruit shape in longitudinal section, a green ground color of the fruit skin with medium intensity and a yellowish hue, a small to medium size of the pistil scar, a reddish orange flesh color, and intermediate resistance to powdery mildew *Podosphaera xanthii* (Px) race 1, race 2, race 5, representative seed of which have been deposited under NCIMB Accession No. 42128, or melon variety or cultivar designated 34-765 RZ, as well as seed from such a plant, plant parts of such a plant (such as those mentioned herein) and plants from such seed and/or progeny of such a plant, advantageously progeny exhibiting such combination of such traits, each of which may be within the scope of the invention; such combination of traits may also include andromonoecious sex expression, a strong attachment of the peduncle at maturity, a slow rate of change of fruit color from maturity to overmaturity, and resistance to *Fusarium oxysporum* f. sp. *melonis* race 0, race 1, race 2.

In one embodiment, the invention provides a melon plant which may exhibit a combination of traits including intermediate resistance to powdery mildew *Podosphaera xanthii* (Px) race 1, race 2, race 5, and resistance to *Fusarium oxysporum* f. sp. *melonis* race 0, race 1, race 2.

In one embodiment, the invention provides a melon plant designated 34-765 RZ, representative seed of which have been deposited under NCIMB Accession No. 42128.

In an embodiment of the present invention, there also is provided parts of a melon plant of the invention, which may include parts of a melon plant exhibiting a combination of traits including a medium to dark greyish green color of the young fruit, a circular fruit shape in longitudinal section, a green ground color of the fruit skin with medium intensity and a yellowish hue, a small to medium size of the pistil scar, a reddish orange flesh color, and intermediate resistance to powdery mildew *Podosphaera xanthii* (Px) race 1, race 2, race 5, or parts of a melon plant having any of the aforementioned resistance(s) and a combination of traits including one or more morphological or physiological characteristics tabulated herein, including parts of hybrid melon variety 34-765 RZ, wherein the plant parts are involved in sexual reproduction, which include, without limitation, microspores, pollen, ovaries, ovules, embryo sacs or egg cells and/or wherein the plant parts are suitable for vegetative reproduction, which include, without limitation, cuttings, roots, stems, cells or protoplasts and/or wherein the plant parts are tissue culture of regenerable cells in which the cells or protoplasts of the tissue culture are derived from a tissue such as, for example and without limitation, leaves, pollen, embryos, cotyledon, hypocotyls, meristematic cells, roots, root tips, anthers, flowers, seeds or stems. The plants of the invention from which such parts may come include those wherein representative seed of which has been deposited under NCIMB Accession No. 42128.

In another embodiment there is a plant grown from seeds, representative seed of which having been deposited under NCIMB Accession No. 42128. In a further embodiment there is a plant regenerated from the above-described plant parts or regenerated from the above-described tissue culture. Advantageously such a plant may have morphological and/or physiological characteristics of hybrid melon variety 34-765 RZ and/or of a plant grown from seed, representative seed of which having been deposited under NCIMB Accession No. NCIMB 42128—including without limitation such plants having all of the morphological and physiological characteristics of hybrid melon variety 34-765 RZ and/or of a plant grown from seed, representative seed of which having been deposited under NCIMB Accession No. NCIMB 42128. Accordingly, in still a further embodiment, there is provided a melon plant having all of the morphological and physiological characteristics of hybrid melon variety 34-765 RZ, representative seed of which having been deposited under NCIMB Accession No. 42128. Such a plant may be grown from the seeds, regenerated from the above-described plant parts, or regenerated from the above-described tissue culture. A melon plant having any of the aforementioned resistance(s), and one or more morphological or physiological characteristics recited or tabulated herein, and a melon plant advantageously having all of the aforementioned resistances and the characteristics recited and tabulated herein, are preferred. Parts of such plants—such as those plant parts above-mentioned—are encompassed by the invention.

In one embodiment, there is provided progeny of melon cultivar 34-765 RZ produced by sexual or vegetative reproduction, grown from seeds, regenerated from the above-described plant parts, or regenerated from the above-described tissue culture of the melon cultivar or a progeny plant thereof, representative seed of which having been deposited under NCIMB Accession No. 42128.

Progeny of the hybrid melon variety 34-765 RZ may be modified in one or more other characteristics, in which the modification is a result of, for example and without limitation, mutagenesis or transformation with a transgene.

In still another embodiment, the present invention provides progeny of melon cultivar 34-765 RZ produced by sexual or vegetative reproduction, grown from seeds, regenerated from the above-described plant parts, or regenerated from the above-described tissue culture of the melon cultivar or a progeny plant thereof, in which the regenerated plant shows a combination of traits including a medium to dark greyish green color of the young fruit, a circular fruit shape in longitudinal section, a green ground color of the fruit skin with medium intensity and a yellowish hue, a small to medium size of the pistil scar, a reddish orange flesh color, and intermediate resistance to powdery mildew *Podosphaera xanthii* (Px) race 1, race 2, race 5.

In another embodiment the invention relates to a method of producing an inbred melon plant derived from a plant of the invention of which representative seed has been deposited under NCIMB Accession No. NCIMB 42128, which may comprise of the steps: a) preparing a progeny plant derived from hybrid melon variety 34-765 RZ by crossing a melon plant exhibiting a combination of traits including a medium to dark greyish green color of the young fruit, a circular fruit shape in longitudinal section, a green ground color of the fruit skin with medium intensity and a yellowish hue, a small to medium size of the pistil scar, a reddish orange flesh color, and intermediate resistance to powdery mildew *Podosphaera xanthii* (Px) race 1, race 2, race 5, representative seed of which have been deposited under NCIMB Accession No. 42128 with a second melon plant; b) crossing the progeny plant with itself or a second melon plant to produce a seed of a progeny plant of a subsequent generation; c) growing a progeny plant of a subsequent generation from said seed and crossing the progeny plant of a subsequent generation with itself or a second melon plant; and d) repeating step b) or c) for at least 1 more generation to produce an inbred melon plant derived from the hybrid melon variety 34-765 RZ.

The invention even further relates to a method of producing melon fruits which may comprise: (a) cultivating the hybrid melon variety 34-765 RZ, representative seed of which having been deposited under NCIMB Accession No. NCIMB 42128, to produce fruits and; (b) harvesting melon fruits from the plant. The invention further comprehends the fruit itself, optionally in processed or packed form.

Accordingly, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. §112, first paragraph) or the EPO (Article 83 of the EPC), such that Applicants reserve the right and hereby disclose a disclaimer of any previously described product, process of making the product, or method of using the product.

It is noted that in this disclosure and particularly in the claims, terms such as "comprises", "comprised", and "comprising" and the like (e.g., "includes", "included", "including", "contains", "contained", "containing", "has", "had", "having", etc.) can have the meaning ascribed to them in US patent law, i.e., they are open ended terms. For example, any method that "comprises," "has" or "includes" one or more steps is not limited to possessing only those one or more steps and also covers other unlisted steps. Similarly, any plant that "comprises," "has" or "includes" one or more traits is not limited to possessing only those one or more traits and covers other unlisted traits. Similarly, the terms "consists essentially of" and "consisting essentially of" have the meaning ascribed to them in US patent law, e.g., they allow for elements not explicitly recited, but exclude elements that are found in the prior art or that affect a basic or novel characteristic of the invention. See also MPEP §2111.03. In addition, the term "about" is used to indicate that a value includes the standard deviation of error for the device or method being employed to determine the value.

These and other embodiments are disclosed or are obvious from and encompassed by the following Detailed Description.

DEPOSIT

The Deposit with NCIMB Ltd, Ferguson Building, Craibstone Estate, Bucksburn, Aberdeen AB21 9YA, UK, on 13 Mar. 2013, under deposit accession number NCIMB 42128 was made pursuant to the terms of the Budapest Treaty. Upon issuance of a patent, all restrictions upon the deposit will be removed, and the deposit is intended to meet the requirements of 37 CFR §1.801-1.809. The deposit will be maintained in the depository for a period of 30 years, or 5 years after the last request, or for the effective life of the patent, whichever is longer, and will be replaced if necessary during that period.

DETAILED DESCRIPTION OF THE INVENTION

The invention provides methods and compositions relating to plants, seeds and derivatives of a new hybrid melon variety herein referred to as hybrid melon variety 34-765 RZ. 34-765 RZ is a hybrid plant variety that is uniform and distinct from other such hybrids, and may be stably produced after a cycle of reproduction.

There are numerous steps in the development of any novel plant with desirable characteristics. Selection of traits is a very important aspect of plant breeding. Once desirable traits are identified, the plants with those desirable traits are crossed in order to recombine the desirable traits and through selection, varieties or parent lines are developed. The goal is to combine in a single variety or hybrid an improved combination of desirable traits from the parent plant or plants. These important traits may include but are not limited to higher yield, field performance, fruit and agronomic quality such as fruit shape, color and length, resistance to diseases and insects, and tolerance to drought and heat.

Choice of breeding or selection methods depends on the mode of plant reproduction, the heritability of the trait(s) being improved, and the type of cultivar used commercially (e.g., F1 hybrid cultivar, pureline cultivar, etc.). Popular selection methods commonly include but are not limited to pedigree selection, modified pedigree selection, mass selection, and recurrent selection.

The complexity of inheritance influences choice of the breeding method. Backcross breeding is used to transfer one or a few favorable genes coding for a highly heritable trait into a desirable cultivar. This approach is used extensively for breeding disease-resistant cultivars. Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

The development of commercial melon hybrids relates to the development of melon parental lines, the crossing of these lines, and the evaluation of the crosses. Pedigree breeding and recurrent selection breeding methods are used to develop cultivars from breeding populations. Breeding programs combine desirable traits from two or more varieties or various broad-based sources into breeding pools from which lines are developed by selfing and selection of desired phenotypes. The new lines are crossed with other lines and the hybrids from these crosses are evaluated to determine which have the desirable characteristics.

Pedigree breeding is used commonly for the improvement and development of inbred lines of self-pollinating or cross-pollinating crops. Two parents which possess favorable, complementary traits are crossed to produce an F1. An F2 population is produced by selfing one or several F1s or by intercrossing two F1s (sib mating). Selection of the best individuals is usually begun in the F2 population; then, beginning in the F3, generally the best individuals in the best families are selected. Replicated testing of families, or hybrid combinations involving individuals of these families, often follows in the F4 generation to improve the effectiveness of selection for traits with low heritability. At an advanced stage of inbreeding suitable lines are used as parents to produce F1 hybrids, which are subsequently tested for potential release as new varieties or cultivars.

Mass and recurrent selections may be used to improve populations of either self- or cross-pollinating crops. A genetically variable population of heterozygous individuals is either identified or created by intercrossing several different parents. The best plants are selected based on individual superiority, outstanding progeny, or excellent combining ability. The selected plants are intercrossed to produce a new population in which further cycles of selection are continued.

Backcross breeding has been used to transfer genes for a simply inherited, highly heritable trait into a desirable homozygous cultivar or line that is the recurrent parent. The source of the trait to be transferred is called the donor parent. The resulting plant is expected to have the attributes of the recurrent parent (e.g. the cultivar or parent line) and the desirable trait transferred from the donor parent. After the initial cross, individuals possessing the phenotype of the donor parent for the preferred trait are selected and repeatedly crossed (backcrossed) to the recurrent parent. The resulting plant is expected to have the attributes of the recurrent parent (e.g. the cultivar or parent line) and the desirable trait transferred from the donor parent.

Other methods of breeding may also relate to the single-seed descent procedure which refers to planting a segregating population, harvesting a sample of one seed per plant, and using the one-seed sample to plant the next generation. When the population has been advanced from the F2 to the desired level of inbreeding, the plants from which lines are derived will each trace to different F2 individuals. The number of plants in a population declines each generation due to failure of some seeds to germinate or some plants to produce at least one seed. As a result, not all of the F2 plants originally sampled in the population will be represented by a progeny when generation advance is completed.

In addition to phenotypic observations, the genotype of a plant may also be examined. There are many laboratory-based techniques available for the analysis, comparison and characterization of plant genotype; these techniques include but are not limited to Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length polymorphisms (AFLPs), Simple Sequence Repeats (SSRs—which are also referred to as Microsatellites), and Single Nucleotide Polymorphisms (SNPs)

Isozyme Electrophoresis and RFLPs have been widely used to determine genetic composition. Shoemaker and Olsen, (Molecular Linkage Map of Soybean (*Glycine max*) p 6.131-6.138 in S. J. O'Brien (ed) Genetic Maps: Locus Maps of Complex Genomes, Cold Spring Harbor Laboratory Press, Cold Spring Harbor, N.Y., (1993)) developed a molecular genetic linkage map that consisted of 25 linkage groups with about 365 RFLP, 11 RAPD, three classical markers and four isozyme loci. See also, Shoemaker, R. C., RFLP Map of Soybean, p 299-309, in Phillips, R. L. and Vasil, I. K., eds. DNA-Based Markers in Plants, Kluwer Academic Press, Dordrecht, the Netherlands (1994).

SSR technology is currently the most efficient and practical marker technology; more marker loci may be routinely used and more alleles per marker locus may be found using SSRs in comparison to RFLPs. For example, Diwan and Cregan described a highly polymorphic microsatellite locus in soybean with as many as 26 alleles. (Diwan, N. and Cregan, P. B., Theor. Appl. Genet. 95:22-225, 1997.) SNPs may also be used to identify the unique genetic composition of the invention and progeny varieties retaining that unique genetic composition. Various molecular marker techniques may be used in combination to enhance overall resolution.

Molecular markers, which include markers identified through the use of techniques such as Isozyme Electrophoresis, RFLPs, RAPDs, AP-PCR, DAF, SCARs, AFLPs, SSRs, and SNPs, may be used in plant breeding. One use of molecular markers is Quantitative Trait Loci (QTL) mapping. QTL mapping is the use of markers which are known to be closely linked to alleles that have measurable effects on a quantitative trait. Selection in the breeding process is based upon the accumulation of markers linked to the positive effecting alleles and/or the elimination of the markers linked to the negative effecting alleles from the plant's genome.

Molecular markers may also be used during the breeding process for the selection of qualitative traits. For example, markers closely linked to alleles or markers containing sequences within the actual alleles of interest may be used to select plants that contain the alleles of interest during a backcrossing breeding program. The markers may also be used to select toward the genome of the recurrent parent and against the markers of the donor parent. This procedure attempts to minimize the amount of genome from the donor parent that remains in the selected plants. It may also be used to reduce the number of crosses back to the recurrent parent needed in a backcrossing program. The use of molecular markers in the selection process is often called genetic marker enhanced selection or marker-assisted selection. Molecular markers may also be used to identify and exclude certain sources of germplasm as parental varieties or ancestors of a plant by providing a means of tracking genetic profiles through crosses.

Mutation breeding is another method of introducing new traits into melon varieties. Mutations that occur spontaneously or are artificially induced may be useful sources of variability for a plant breeder. The goal of artificial mutagenesis is to increase the rate of mutation for a desired characteristic. Mutation rates may be increased by many different means including temperature, long-term seed storage, tissue culture conditions, radiation (such as X-rays, Gamma rays, neutrons, Beta radiation, or ultraviolet radiation), chemical mutagens (such as base analogs like 5-bromo-uracil), antibiotics, alkylating agents (such as sulfur mustards, nitrogen mustards, epoxides, ethyleneamines, sulfates, sulfonates, sulfones, or lactones), azide, hydroxylamine, nitrous acid or acridines. Once a desired trait is observed through mutagenesis the trait may then be incorporated into existing germplasm by traditional breeding techniques. Details of mutation breeding may be found in Principles of Cultivar Development by Fehr, Macmillan Publishing Company, 1993.

The production of doubled haploids may also be used for the development of homozygous lines in a breeding program. Doubled haploids are produced by the doubling of one set of chromosomes from a heterozygous plant to produce a completely homozygous individual. For example, see Wan et al., Theor. Appl. Genet., 77:889-892, 1989

The melon plant of the invention may be arrived at through crossing of inbred lines or through selection of the disclosed desirable characteristics by any of the breeding and selection methods mentioned above.

Hybrid melon variety 34-765 RZ is a cross between two uniform parent lines. The female line, ME5 780, is obtained from NS 7455 after a process of selfing and selection over eight generations. The female line was selected and evaluated in De Lier, the Netherlands. The male line is a Doubled-Haploid line from the variety Globestar. The line was selected and selfed in Aramon, France. The first cross between the parent lines was made in 2008. The hybrid was selected in view of its rather small fruits (0.8-1 Kg), uniform size and dense net. Internal quality is very good, nice dark orange flesh colour and a great flavor.

In one embodiment, a plant of the invention has all the morphological and physiological characteristics of melon variety 34-765 RZ. These characteristics of a melon plant of the invention, e.g. variety 34-765 RZ, are summarized in Table 1, together with the characteristics of a comparable publicly available variety, Caribbean Gold, which is used as comparison.

The information presented in Table 1 was determined in trial experiments in accordance with official Dutch plant variety registration authorities (Naktuinbouw). The terminology used in the Table 1 is the official terminology as used by the Dutch plant variety registration authorities (Naktuinbouw) as of the filing date, and is thus clear for a person skilled in the art.

The terminology and descriptors used by the Naktuinbouw, and accordingly in Table 1, are in line with the descriptors of the "UPOV Guidelines for the Conduct of Tests for Distinctness, Uniformity, and Stability", or the "Test Guidelines" for *Cucumis melo*. The "Test Guidelines" indicate reference varieties for all the descriptors or characteristics that are included in the list. Test guidelines for all crops may be accessed through the UPOV website, at http://www.upov.int/test guidelines/en/index.jsp. For melon, the most recent english Test Guideline TG/104/5, including reference varieties, was updated in 2006, and is accessible at http://www.upov.int/edocs/tgdocs/en/tg104.pdf.

In addition the "Calibration book of *Cucumis melo* L.—Melon" (NAKTuinbouw, 2010) provides even more detailed reference information on most of the characteristics that are included in Table 1.

As used herein resistances against *Fusarium oxysporum* f. sp. *melonis* (Fom), powdery mildew *Podosphaera xanthii* (Px), powdery mildew *Golovinomyces cichoracearum* (Gc), and against *Aphis gossypii* (aphids) are determined in accordance with the protocol as described in the UPOV "Test Guidelines" TG/104/5 for *Cucumis melo.*

Embodiments of the invention advantageously have one or more, and most advantageously all, of these characteristics.

TABLE 1

Physiological and morphological characteristics of hybrid melon variety 34-765 RZ and comparison variety Caribbean Gold.
Variety description information for 34-765 RZ and comparison variety Caribbean Gold

| | 34-765 RZ | | Caribbean Gold F1 | |
|---|---|---|---|---|
| CPVO Characteristics | States of expression | Note | States of expression | Note |
| 2 Seedling: size of cotyledon | small to medium | 4 | small | 3 |
| 4 Leaf blade: size | medium | 5 | medium to large | 6 |
| 5 Leaf blade: intensity of green colour | medium to dark | 6 | dark | 7 |
| 6 Leaf blade: development of lobes | medium | 5 | weak to medium | 4 |
| 7 Leaf blade: length of terminal lobe | medium | 5 | short to medium | 4 |
| 11 Petiole: length | medium | 5 | medium to long | 6 |
| 12 Inflorescence: sex expression (at full flowering) | andromonoecious | 2 | monoecious | 1 |
| 13 Young fruit: hue of green colour of skin | greyish green | 4 | greyish green | 4 |
| 14 Young fruit: intensity of green colour of skin | medium to dark | 6 | very light to light | 2 |
| 18 Young fruit: conspicuousness of groove colouring | absent | 1 | absent or very weak | 1 |
| 21 Young fruit: thickness of peduncle 1 cm from fruit | medium | 5 | medium | 5 |

TABLE 1-continued

Physiological and morphological characteristics of hybrid melon variety 34-765 RZ and comparison variety Caribbean Gold.
Variety description information for 34-765 RZ and comparison variety Caribbean Gold

| | 34-765 RZ | | Caribbean Gold F1 | |
|---|---|---|---|---|
| CPVO Characteristics | States of expression | Note | States of expression | Note |
| 23 Fruit: change of skin colour from young fruit to maturity | late in fruit development | 2 | very late in fruit development or no change | 3 |
| 24 Fruit: length | medium | 5 | long | 7 |
| 25 Fruit: diameter | narrow to medium | 4 | medium to broad | 6 |
| 26 Fruit: ratio length/diameter | small | 3 | medium to large | 6 |
| 27 Fruit: position of maximum diameter | at middle | 2 | at middle | 2 |
| 28 Fruit: shape in longitudinal section | circular | 4 | medium elliptic (to ovate) | 2 |
| 29 Fruit: ground colour of skin | green | 3 | grey | 4 |
| 30 Fruit: intensity of ground colour of skin | medium | 5 | light to medium | 4 |
| 31 Fruit: hue of ground colour of skin | yellowish | 3 | greenish | 6 |
| 36 Fruit: density of patches | absent or very sparse | 1 | absent or very sparse | 1 |
| 38 Fruit: warts | absent | 1 | absent | 1 |
| 39 Fruit: strength of attachment of peduncle at maturity | strong | 7 | medium to strong | 6 |
| 40 Fruit: shape of base | rounded | 2 | rounded | 2 |
| 41 Fruit: shape of apex | rounded | 2 | rounded | 2 |
| 42 Fruit: size of pistil scar | small to medium | 4 | medium | 5 |
| 43 Fruit: grooves | absent | 1 | absent or very weakly expressed | 1 |
| 47 Fruit: creasing of surface | absent | 1 | absent or very weak | 1 |
| 48 Fruit: cork formation | present | 9 | present | 9 |
| 49 Fruit: thickness of cork layer | medium | 5 | medium to thick | 6 |
| 50 Fruit: pattern of cork formation | netted only | 5 | netted only | 5 |
| 51 Fruit: density of pattern of cork formation | dense | 7 | medium to dense | 6 |
| 52 Fruit: rate of change of skin colour from maturity to overmaturity | slow | 3 | absent or very slow | 1 |
| 53 Fruit: width of flesh in longitudinal section (at position of maximum fruit diameter) | medium to thick | 6 | medium | 5 |
| 54 Fruit: main colour of flesh | reddish orange | 6 | orange | 5 |
| 59 Seed: length | medium | 5 | medium | 5 |
| 60 Seed: width | medium | 5 | medium | 5 |
| 61 Seed: shape | not pine-nut shape | 1 | not pine-nut shape | 1 |
| 62 Seed: color | cream yellow | 2 | cream yellow | 2 |
| 63 Only varieties with cream yellow seed colour Seed: intensity of color | light to medium | 4 | light to medium | 4 |
| 64 Time of male flowering | medium | 5 | early | 3 |
| 65 Time of female flowering | medium | 5 | early | 3 |
| 66 Time of ripening | medium | 5 | medium to late | 6 |
| 67 Shelf life of fruit | medium | 5 | long | 7 |
| 68.1 Resistance to *Fusarium oxysporum* f. sp. *melonis*: Race 0 | present | 9 | present | 9 |
| 68.2 Resistance to *Fusarium oxysporum* f. sp. *melonis*: Race 1 | present | 9 | present | 9 |
| 68.3 Resistance to *Fusarium oxysporum* f. sp. *melonis*: Race 2 | present | 9 | present | 9 |
| 69.1 Resistance to *Sphaerotheca fuliginea* (*Podosphaera xanthii*) (Powdery mildew): race 1 | intermediate resistant | 2 | intermediate resistant | 2 |
| 69.2 Resistance to *Sphaerotheca fuliginea* (*Podosphaera xanthii*) (Powdery mildew): race 2 | intermediate resistant | 2 | intermediate resistant | 2 |
| 69.3 Resistance to *Sphaerotheca fuliginea* (*Podosphaera xanthii*) (Powdery mildew): race 5 | intermediate resistant | 2 | absent | 1 |
| 71 Resistance to colonization by *Aphis gossypii* | absent | 1 | present | 9 |

In an embodiment, the invention relates to melon plants that have all the morphological and physiological characteristics of the invention and have acquired said characteristics by introduction of the genetic information that is responsible for the characteristics from a suitable source, either by conventional breeding, or genetic modification, in particular by cisgenesis or transgenesis. Cisgenesis is genetic modification of plants with a natural gene, coding for an (agricultural) trait, from the crop plant itself or from a sexually compatible donor plant. Transgenesis is genetic modification of a plant with a gene from a non-crossable species or a synthetic gene.

Just as useful traits that may be introduced into a hybrid by backcrossing the trait into one or both parents, useful traits may be introduced directly into the plant of the invention, being a plant of hybrid melon variety 34-765 RZ, by genetic transformation techniques; and, such plants of hybrid melon variety 34-765 RZ that have additional genetic information introduced into the genome or that express additional traits by having the DNA coding therefore introduced into the genome via transformation techniques, are within the ambit of the invention, as well as uses of such plants, and the making of such plants.

Genetic transformation may therefore be used to insert a selected transgene into the plant of the invention, being a plant of hybrid melon variety 34-765 RZ or may, alternatively, be used for the preparation of transgenes which may be introduced by backcrossing. Methods for the transformation of plants, including melon, are well known to those of skill in the art.

Vectors used for the transformation of melon cells are not limited so long as the vector may express an inserted DNA in the cells. For example, vectors which may comprise promoters for constitutive gene expression in melon cells (e.g., cauliflower mosaic virus 35S promoter) and promoters inducible by exogenous stimuli may be used. Examples of suitable vectors include pBI binary vector. The "melon cell" into which the vector is to be introduced includes various forms of melon cells, such as cultured cell suspensions, protoplasts, leaf sections, and callus. A vector may be introduced into melon cells by known methods, such as the polyethylene glycol method, polycation method, electroporation, *Agrobacterium*-mediated transfer, particle bombardment and direct DNA uptake by protoplasts. To effect transformation by electroporation, one may employ either friable tissues, such as a suspension culture of cells or embryogenic callus or alternatively one may transform immature embryos or other organized tissue directly. In this technique, one would partially degrade the cell walls of the chosen cells by exposing them to pectin-degrading enzymes (pectolyases) or mechanically wound tissues in a controlled manner.

A particularly efficient method for delivering transforming DNA segments to plant cells is microprojectile bombardment. In this method, particles are coated with nucleic acids and delivered into cells by a propelling force. Exemplary particles include those comprised of tungsten, platinum, and preferably, gold. For the bombardment, cells in suspension are concentrated on filters or solid culture medium. Alternatively, immature embryos or other target cells may be arranged on solid culture medium. The cells to be bombarded are positioned at an appropriate distance below the macroprojectile stopping plate. An illustrative embodiment of a method for delivering DNA into plant cells by acceleration is the Biolistics Particle Delivery System, which may be used to propel particles coated with DNA or cells through a screen, such as a stainless steel or Nytex screen, onto a surface covered with target melon cells. The screen disperses the particles so that they are not delivered to the recipient cells in large aggregates. It is believed that a screen intervening between the projectile apparatus and the cells to be bombarded reduces the size of projectiles aggregate and may contribute to a higher frequency of transformation by reducing the damage inflicted on the recipient cells by projectiles that are too large. Microprojectile bombardment techniques are widely applicable, and may be used to transform virtually any plant species, including a plant of melon variety 34-765 RZ.

*Agrobacterium*-mediated transfer is another widely applicable system for introducing gene loci into plant cells. An advantage of the technique is that DNA may be introduced into whole plant tissues, thereby bypassing the need for regeneration of an intact plant from a protoplast. *Agrobacterium* transformation vectors are capable of replication in *E. coli* as well as *Agrobacterium*, allowing for convenient manipulations. Moreover, advances in vectors for *Agrobacterium*-mediated gene transfer have improved the arrangement of genes and restriction sites in the vectors to facilitate the construction of vectors capable of expressing various polypeptide coding genes. The vectors have convenient multi-linker regions flanked by a promoter and a polyadenylation site for direct expression of inserted polypeptide coding genes. Additionally, *Agrobacterium* containing both armed and disarmed Ti genes may be used for transformation. In those plant strains where *Agrobacterium*-mediated transformation is efficient, it is the method of choice because of the facile and defined nature of the gene locus transfer. The use of *Agrobacterium*-mediated plant integrating vectors to introduce DNA into plant cells, including melon plant cells, is well known in the art (See, e.g., U.S. Pat. Nos. 7,250,560 and 5,563,055).

Transformation of plant protoplasts also may be achieved using methods based on calcium phosphate precipitation, polyethylene glycol treatment, electroporation, and combinations of these treatments.

A number of promoters have utility for plant gene expression for any gene of interest including but not limited to selectable markers, scoreable markers, genes for pest tolerance, disease resistance, nutritional enhancements and any other gene of agronomic interest. Examples of constitutive promoters useful for melon plant gene expression include, but are not limited to, the cauliflower mosaic virus (CaMV) P-35S promoter, a tandemly duplicated version of the CaMV 35S promoter, the enhanced 35S promoter (P-e35S), the nopaline synthase promoter, the octopine synthase promoter, the figwort mosaic virus (P-FMV) promoter (see U.S. Pat. No. 5,378,619), an enhanced version of the FMV promoter (P-eFMV) where the promoter sequence of P-FMV is duplicated in tandem, the cauliflower mosaic virus 19S promoter, a sugarcane bacilliform virus promoter, a commelina yellow mottle virus promoter, the promoter for the thylakoid membrane proteins from melon (psaD, psaF, psaE, PC, FNR, atpC, atpD, cab, rbcS) (see U.S. Pat. No. 7,161,061), the CAB-1 promoter from melon (see U.S. Pat. No. 7,663,027), the promoter from maize prolamin seed storage protein (see U.S. Pat. No. 7,119,255), and other plant DNA virus promoters known to express in plant cells. A variety of plant gene promoters that are regulated in response to environmental, hormonal, chemical, and/or developmental signals may be used for expression of an operably linked gene in plant cells, including promoters regulated by (1) heat, (2) light (e.g., pea rbcS-3A promoter, maize rbcS promoter, or chlorophyll a/b-binding protein promoter), (3) hormones, such as abscisic acid, (4) wounding (e.g., wunl, or (5) chemicals such as methyl jasmonate, salicylic acid, or Safener. It may also be advantageous to employ organ-specific promoters.

Exemplary nucleic acids which may be introduced to the melon variety of this invention include, for example, DNA sequences or genes from another species, or even genes or sequences which originate from or are present in melon species, but are incorporated into recipient cells by genetic engineering methods rather than classical reproduction or breeding techniques. However, the term "exogenous" is also intended to refer to genes that are not normally present in the cell being transformed, or perhaps simply not present in the form, structure, etc., as found in the transforming DNA segment or gene, or genes which are normally present and that one desires to express in a manner that differs from the natural expression pattern, e.g., to over-express. Thus, the term "exogenous" gene or DNA is intended to refer to any gene or DNA segment that is introduced into a recipient cell, regardless of whether a similar gene may already be present in such a cell. The type of DNA included in the exogenous DNA may include DNA which is already present in the plant cell, DNA from another plant, DNA from a different organism, or a DNA generated externally, such as a DNA sequence containing an antisense message of a gene, or a DNA sequence encoding a synthetic or modified version of a gene.

Many hundreds if not thousands of different genes are known and could potentially be introduced into a plant of melon variety 34-765 RZ. Non-limiting examples of particular genes and corresponding phenotypes one may choose to introduce into a melon plant include one or more genes for insect tolerance, pest tolerance such as genes for fungal disease control, herbicide tolerance, and genes for quality improvements such as yield, nutritional enhancements, environmental or stress tolerances, or any desirable changes in plant physiology, growth, development, morphology or plant product(s).

Alternatively, the DNA coding sequences may affect these phenotypes by encoding a non-translatable RNA molecule that causes the targeted inhibition of expression of an endogenous gene, for example via antisense- or cosuppression-mediated mechanisms. The RNA could also be a catalytic RNA molecule (i.e., a ribozyme) engineered to cleave a desired endogenous mRNA product. Thus, any gene which produces a protein or mRNA which expresses a phenotype or morphology change of interest is useful for the practice of the present invention. (See also U.S. Pat. No. 7,576,262, "Modified gene-silencing RNA and uses thereof.")

U.S. Pats. Nos. 7,230,158, 7,122,720, 7,081,363, 6,734,341, 6,503,732, 6,392,121, 6,087,560, 5,981,181, 5,977,060, 5,608,146, 5,516,667, each of which, and all documents cited therein are hereby incorporated herein by reference, consistent with the above INCORPORATION BY REFERENCE section, are additionally cited as examples of U.S. patents that may concern transformed melon and/or methods of transforming melon or melon plant cells, and techniques from these US patents, as well as promoters, vectors, etc., may be employed in the practice of this invention to introduce exogenous nucleic acid sequence(s) into a plant of melon variety 34-765 RZ (or cells thereof), and exemplify some exogenous nucleic acid sequence(s) which may be introduced into a plant of melon variety 34-765 RZ (or cells thereof) of the invention, as well as techniques, promoters, vectors etc., to thereby obtain further plants of melon variety 34-765 RZ, plant parts and cells, seeds, other propagation material, harvestable parts of these plants, etc. of the invention, e.g. tissue culture, including a cell or protoplast, such as an embryo, meristem, cotyledon, pollen, leaf, anther, root, root tip, pistil, flower, seed or stalk.

The invention further relates to propagation material for producing plants of the invention. Such propagation material may comprise inter alia seeds of the claimed plant and parts of the plant that are involved in sexual reproduction. Such parts are for example selected from the group consisting of seeds, microspores, pollen, ovaries, ovules, embryo sacs and egg cells. In addition, the invention relates to propagation material which may comprise parts of the plant that are suitable for vegetative reproduction, for example cuttings, roots, stems, cells, protoplasts.

According to a further aspect thereof the propagation material of the invention may comprise a tissue culture of the claimed plant. The tissue culture may comprise regenerable cells. Such tissue culture may be derived from leaves, pollen, embryos, cotyledon, hypocotyls, meristematic cells, roots, root tips, anthers, flowers, seeds and stems. Tissue culture methodologies relating to melon plants are well known in the art (P. P. Chee, HortScience 26(7): 908-910 (1991); J. F. Reynolds. 14. In vitro culture of vegetable crops. Chapter 12.1 Melon. In: I. K. Vasil: Plant Cell and Tissue Culture: 349-351 (1994)).

Also, the invention comprehends methods for producing a seed of a "34-765 RZ"-derived melon plant which may comprise (a) crossing a plant of melon variety 34-765 RZ, representative seed of which having been deposited under NCIMB Accession No. NCIMB 42128, with a second melon plant, and (b) whereby seed of a "34-765 RZ"-derived melon plant form (e.g., by allowing the plant from the cross to grow to produce seed). Such a method may further comprise (c) crossing a plant grown from "34-765 RZ"-derived melon seed with itself or with a second melon plant to yield additional "34-765 RZ"-derived melon seed, (d) growing the additional "34-765 RZ"-derived melon seed of step (c) to yield additional "34-765 RZ"-derived melon plants, and (e) repeating the crossing and growing of steps (c) and (d) for an additional 3-10 generations to further generate "34-765 RZ"-derived melon plants.

The invention additionally provides a method of introducing a desired trait into a plant of hybrid melon variety 34-765 RZ by reverse breeding (See generally allowed U.S. application Ser. No. 10/487,468, published as 2006-0179498 A1), which may comprise the following steps: (a) allowing the hybrid melon plant to produce haploid cells, while suppressing recombination, (b) growing haploid cells into diploid plants, (c) selecting those homozygous plants which together constitute the hybrid variety of the invention as parent plants for the said hybrid, (d) crossing one of the said parent plants with a plant having the desired trait, (e) crossing the selected F1 progeny with said parent plant, to produce backcross progeny, (f) selecting backcross progeny which may comprise the desired trait and the physiological and morphological characteristic of the parent plant; and, optionally, (g) repeating steps (e) and (f) one or more times in succession to produce selected fourth or higher backcross progeny that comprise the desired trait and all of the physiological and morphological characteristics of said parent plant, (h) crossing the backcrossed parent plant having the added desired trait with the other parent plant obtained after reverse breeding to obtain a plant which may comprise the desired trait and all of the physiological and morphological characteristics of a plant of melon variety 34-765 RZ.

Backcrossing one of the parents of a hybrid may also be used to improve an inbred plant. Backcrossing transfers a specific desirable trait from one inbred or non-inbred source to an inbred that lacks that trait. This may be accomplished, for example, by first crossing a superior inbred (A) (recurrent parent) to a donor inbred (non-recurrent parent), which carries the appropriate locus or loci for the trait in question. The progeny of this cross are then mated back to the superior recurrent parent (A) followed by selection in the resultant progeny for the desired trait to be transferred from the non-recurrent parent. After five or more backcross generations with selection for the desired trait, the progeny are heterozygous for loci controlling the characteristic being transferred, but are like the superior parent for most or almost all other loci. The last backcross generation would be selfed to give pure breeding progeny for the trait being transferred.

The invention further involves a method of determining the genotype of a plant of melon variety 34-765 RZ, representative seed of which has been deposited under NCIMB Accession No. NCIMB 42128, or a first generation progeny thereof, which may comprise obtaining a sample of nucleic acids from said plant and comparing said nucleic acids to a sample of nucleic acids obtained from a reference plant, and detecting a plurality of polymorphisms between the two nucleic acid samples. This method may additionally comprise the step of storing the results of detecting the plurality of polymorphisms on a computer readable medium. The plurality of polymorphisms are indicative of and/or give rise to the expression of one or more, or all, of the morphological and physiological characteristics of melon variety 34-765 RZ.

The polymorphisms of this invention may be provided in a variety of mediums to facilitate use, e.g. a database or computer readable medium, which may also contain descriptive annotations in a form that allows a skilled artisan to examine or query the polymorphisms and obtain useful information.

As used herein “database” refers to any representation of retrievable collected data including computer files such as text files, database files, spreadsheet files and image files, printed tabulations and graphical representations and combinations of digital and image data collections. In a preferred aspect of the invention, “database” refers to a memory system that may store computer searchable information.

As used herein, “computer readable media” refers to any medium that may be read and accessed directly by a computer. Such media include, but are not limited to: magnetic storage media, such as floppy discs, hard disc, storage medium and magnetic tape; optical storage media such as CD-ROM; electrical storage media such as RAM, DRAM, SRAM, SDRAM, ROM; and PROMs (EPROM, EEPROM, Flash EPROM), and hybrids of these categories such as magnetic/optical storage media. A skilled artisan may readily appreciate how any of the presently known computer readable mediums may be used to create a manufacture which may comprise computer readable medium having recorded thereon a polymorphism of the present invention.

As used herein, “recorded” refers to the result of a process for storing information in a retrievable database or computer readable medium. For instance, a skilled artisan may readily adopt any of the presently known methods for recording information on computer readable medium to generate media which may comprise the polymorphisms of the present invention. A variety of data storage structures are available to a skilled artisan for creating a computer readable medium where the choice of the data storage structure will generally be based on the means chosen to access the stored information. In addition, a variety of data processor programs and formats may be used to store the polymorphsims of the present invention on computer readable medium.

The present invention further provides systems, particularly computer-based systems, which contain the polymorphisms described herein. Such systems are designed to identify the polymorphisms of this invention. As used herein, “a computer-based system” refers to the hardware, software and memory used to analyze the polymorphisms. A skilled artisan may readily appreciate that any one of the currently available computer-based system are suitable for use in the present invention.

The invention is further described by the following numbered paragraphs:

1. A melon plant exhibiting a combination of traits comprising a medium to dark greyish green color of the young fruit, a circular fruit shape in longitudinal section, a green ground color of the fruit skin with medium intensity and a yellowish hue, a small to medium size of the pistil scar, a reddish orange flesh color, and intermediate resistance to powdery mildew *Podosphaera xanthii* (Px) race 1, race 2, race 5, representative seed of which having been deposited under NCIMB Accession No. 42128.

2. The melon plant of paragraph 1 wherein said combination of traits further comprises andromonoecious sex expression, a strong attachment of the peduncle at maturity, a slow rate of change of fruit color from maturity to overmaturity, and resistance to *Fusarium oxysporum* f. sp. *melonis* race 0, race 1, race 2.

3. A melon plant designated 34-765 RZ, representative seed of which having been deposited under NCIMB Accession No. 42128.

4. A seed of the plant of paragraph 1 or paragraph 2.

5. Parts of the plant of paragraph 1 or paragraph 2 or paragraph 3, wherein said parts of the plant are suitable for sexual reproduction.

6. Parts of the plant of paragraph 5, said parts selected from the group consisting of microspores, pollen, ovaries, ovules, embryo sacs and egg cells.

7. Parts of the plant of paragraph 1 or paragraph 2 or paragraph 3, wherein said parts of the plant are suitable for vegetative reproduction.

8. Parts of paragraph 7, said parts selected from the group consisting of cuttings, roots, stems, cells and protoplasts.

9. A tissue culture of regenerable cells from the melon plant of paragraph 1 or paragraph 2 or paragraph 3.

10. The tissue culture of paragraph 9, wherein said cells or protoplasts of the tissue culture are derived from a tissue selected from the group consisting of leaves, pollen, embryos, cotyledon, hypocotyls, meristematic cells, roots, root tips, anthers, flowers, seeds and stems.

11. A progeny of a melon plant of paragraph 1 or paragraph 2 or paragraph 3.

12. The progeny of paragraph 11, wherein said progeny is produced by sexual or vegetative reproduction of said melon plant, and wherein said progeny exhibits a combination of traits comprising a medium to dark greyish green color of the young fruit, a circular fruit shape in longitudinal section, a green ground color of the fruit skin with medium intensity and a yellowish hue, a small to medium size of the pistil scar, a reddish orange flesh color, and intermediate resistance to powdery mildew *Podosphaera xanthii* (Px) race 1, race 2, race 5.

13. A progeny of a melon plant of paragraph 3, having all the morphological and physiological characteristics of the melon plant of paragraph 3, representative seed of which having been deposited under NCIMB Accession No. 42128 wherein the morphological and physiological characteristics are as found in melon variety 34-765 RZ, representative seed of which having been deposited under NCIMB Accession No. 42128.

14. A progeny of a melon plant of paragraph 1 or paragraph 2 or paragraph 3, representative seed of which having been deposited under NCIMB Accession 42128, which progeny is modified in one or more other characteristics.

15. The progeny of paragraph 14, wherein the modification is effected by mutagenesis.

16. The progeny of paragraph 14, wherein the modification is effected by transformation with a transgene.

17. A method of producing an inbred melon plant derived from hybrid melon variety 34-765 RZ, comprising the steps:

a) preparing a progeny plant derived from hybrid melon variety 34-765 RZ by crossing the plant of paragraph 1 or paragraph 2 with a second melon plant;

b) crossing the progeny plant with itself or a second melon plant to produce a seed of a progeny plant of a subsequent generation;

c) growing a progeny plant of a subsequent generation from said seed and crossing the progeny plant of a subsequent generation with itself or a second melon plant; and d) repeating step b) or c) for at least 1 more generation to produce an inbred melon plant derived from the hybrid melon variety 34-765 RZ.

18. An inbred melon plant produced by the method of paragraph 17.

19. A method of producing a melon fruit comprising: (a) obtaining a plant according to paragraph 1 or paragraph 2, wherein the plant has been cultivated to develop fruit; and (b) collecting a melon fruit from the plant.

20. A fruit produced by the method of paragraph 19.

21. A method for producing a seed of a 34-765 RZ-derived melon plant comprising (a) crossing a plant of melon variety 34-765 RZ, representative seed of which having been deposited under NCIMB Accession No. NCIMB 42128, with a second melon plant, and (b) whereby seed of a 34-765 RZ-derived melon plant forms.

22. The method of paragraph 21 further comprising (c) crossing a plant grown from 34-765 RZ-derived melon seed with itself or with a second melon plant to yield additional 34-765 RZ-derived melon seed, (d) growing the additional 34-765 RZ-derived melon seed of step (c) to yield additional 34-765 RZ-derived melon plants, and (e) repeating the crossing and growing of steps (c) and (d) for an additional 3-10 generations to generate further 34-765 RZ-derived melon plants.

23. The method of paragraph 21 or paragraph 22 wherein the 34-765 RZ-derived melon plant exhibits a combination of traits comprising a medium to dark greyish green color of the young fruit, a circular fruit shape in longitudinal section, a green ground color of the fruit skin with medium intensity and a yellowish hue, a small to medium size of the pistil scar, a reddish orange flesh color, and intermediate resistance to powdery mildew *Podosphaera xanthii* (Px) race 1, race 2, race 5.

24. Seed produced by the method of paragraph 21 or paragraph 22 or paragraph 23.

25. A method of introducing a desired trait into a parent plant of hybrid melon variety 34-765 RZ comprising: (a) crossing a parent plant of hybrid melon variety 34-765 RZ, representative seed of which having been deposited under NCIMB Accession No. NCIMB 42128 with a second melon plant that comprises the desired trait to produce F1 progeny; (b) selecting an F1 progeny that comprises the desired trait; (c) crossing the selected F1 progeny with said parent plant of melon variety 34-765 RZ, to produce backcross progeny and (d) selecting backcross progeny comprising the desired trait and the physiological and morphological characteristics of said parent plant of melon variety 34-765 RZ, when grown in the same environmental conditions.

26. The method of paragraph 25 further comprising: (e) repeating steps (c) and (d) one or more times in succession to produce selected fourth or higher backcross progeny that comprise the desired trait and all of the physiological and morphological characteristics of said parent plant of melon variety 34-765 RZ, when grown in the same environmental conditions.

27. The method of paragraph 25 wherein the parent plant is obtained by reverse breeding.

28. A melon plant produced by the method of paragraph 25 or paragraph 26.

29. A method of determining the genotype of a plant of melon variety 34-765 RZ, representative seed of which has been deposited under NCIMB Accession No. NCIMB 42128, or a first generation progeny thereof, comprising obtaining a sample of nucleic acids from said plant and comparing said nucleic acids to a sample of nucleic acids obtained from a reference plant, and detecting a plurality of polymorphisms between the two nucleic acid samples, wherein the plurality of polymorphisms are indicative of melon variety 34-765 RZ and/or give rise to the expression of any one or more, or all, of the morphological and physiological characteristics of melon variety 34-765 RZ of paragraph 1.

30. The method of paragraph 29 additionally comprising the step of storing the results of detecting the plurality of polymorphisms on a computer readable medium, or transmitting the results of detecting the plurality of polymorphisms.

31. The computer readable medium of paragraph 30.

Having thus described in detail preferred embodiments of the present invention, it is to be understood that the invention is not to be limited to particular details set forth in the above description as many apparent variations thereof are possible without departing from the spirit or scope of the present invention.

What is claimed is:

1. A melon plant exhibiting a combination of traits comprising a medium to dark greyish green color of the young fruit, a circular fruit shape in longitudinal section, a green ground color of the fruit skin with medium intensity and a yellowish hue, a small to medium size of the pistil scar, a reddish orange flesh color, and intermediate resistance to powdery mildew *Podosphaera xanthii* (Px) race 1, race 2, race 5, representative seed of which having been deposited under NCIMB Accession No. 42128.

2. The melon plant of claim 1 wherein said combination of traits further comprises andromonoecious sex expression, a strong attachment of the peduncle at maturity, a slow rate of change of fruit color from maturity to overmaturity, and resistance to *Fusarium oxysporum* f. sp. *melonis* race 0, race 1, race 2.

3. A melon plant designated 34-765 RZ, representative seed of which having been deposited under NCIMB Accession No. 42128.

4. A seed of the plant of claim 1.

5. Parts of the plant of claim 1, wherein said parts of the plant are suitable for sexual reproduction.

6. A part of the plant as claimed in claim 5, said part comprising a microspore, pollen, an ovary, an ovule, an embryo sac or egg cell.

7. A part of the plant of claim 1, wherein said part of the plant is suitable for vegetative reproduction.

8. A part as claimed in claim 7, wherein said part is a cutting, a root, a stem, a cell or a protoplast.

9. A tissue culture of regenerable cells from the melon plant of claim 1.

10. The cell or protoplast of claim 8 derived from a leaf, pollen, an embryo, a cotyledon, a hypocotyl, a meristematic cell, a root, a root tip, an anther, a flower, a seed or a stem.

11. A melon plant exhibiting a combination of traits comprising small leaves with erect to semi-erect petioles, a yellow ground color of the fruit skin, fruits that have a medium rate of change of fruit color from maturity to overmaturity, resistance to aphids (*Aphis gossypii*), intermediate resistance to powdery mildew *Podosphaera xanthii* (Px) race 1, race 2, race 5, intermediate resistance to powdery mildew *Golovinomyces cichoracearum* (Gc) race 1, and having genetic material for so exhibiting the combination of traits; wherein the genetic information is as contained in a plant, representative seed of which having been deposited under NCIMB Accession No. 42128.

12. Progeny of the plant of claim 11, wherein said progeny is produced by sexual or vegetative reproduction of said melon plant, and wherein said progeny exhibits a combination of traits comprising small leaves with erect to semi-erect petioles, a yellow ground color of the fruit skin, fruits that have a medium rate of change of fruit color from maturity to overmaturity, resistance to aphids (*Aphis gossypi*), intermediate resistance to powdery mildew *Podosphaera xanthii* (Px)

race 1, race 2, race 5, and intermediate resistance to powdery mildew *Golovinomyces cichoracearum* (Gc) race 1 and has genetic material for so exhibiting the combination of traits; wherein the genetic information is as contained in a plant, representative seed of which having been deposited under NCIMB Accession No. 42128.

13. A progeny of a melon plant of claim 3, having all the morphological and physiological characteristics of the melon plant of claim 3, representative seed of which having been deposited under NCIMB Accession No. 42128 wherein the morphological and physiological characteristics are as found in melon variety 34-765 RZ, representative seed of which having been deposited under NCIMB Accession No. 42128.

14. A progeny of a melon plant of claim 1, representative seed of which having been deposited under NCIMB Accession 42128, wherein the progeny exhibits the combination of traits of the melon plant of claim 1 and has genetic material for so exhibiting the combination of traits; wherein the genetic information is as contained in a plant, representative seed of which having been deposited under NCIMB Accession No. 42128 and is further modified in one or more other characteristics.

15. The progeny as claimed in claim 14, wherein the modification is effected by mutagenesis.

16. The progeny as claimed in claim 14, wherein the modification is effected by transformation with a transgene.

17. A method of producing an inbred melon plant derived from hybrid melon variety 34-765 RZ, comprising the steps:

a) preparing a progeny plant derived from hybrid melon variety 34-765 RZ by crossing the plant of claim 1 with a second melon plant;

b) crossing the progeny plant with itself or a second melon plant to produce a seed of a progeny plant of a subsequent generation;

c) growing a progeny plant of a subsequent generation from said seed and crossing the progeny plant of a subsequent generation with itself or a second melon plant; and d) repeating step b) or c) for at least 3 more generations to produce an inbred melon plant derived from the hybrid melon variety 34-765 RZ.

18. An inbred melon plant produced by the method of claim 17.

19. A method of producing a melon fruit comprising: (a) obtaining a plant according to claim 1, wherein the plant has been cultivated to develop fruit; and (b) collecting a melon fruit from the plant.

20. A fruit produced by the method of claim 19.

21. A method for producing a seed of a 34-765 RZ-derived melon plant comprising (a) crossing a plant of melon variety 34-765 RZ, representative seed of which having been deposited under NCIMB Accession No. NCIMB 42128, with a second melon plant, and (b) whereby seed of a 34-765 RZ-derived melon plant forms.

22. The method of claim 21 further comprising (c) crossing a plant grown from 34-765 RZ-derived melon seed with itself or with a second melon plant to yield additional 34-765 RZ-derived melon seed, (d) growing the additional 34-765 RZ-derived melon seed of step (c) to yield additional 34-765 RZ-derived melon plants, and (e) repeating the crossing and growing of steps (c) and (d) for an additional 3-10 generations to generate further 34-765 RZ-derived melon plants.

23. The method of claim 21 wherein a 34-765 RZ-derived melon plant exhibits a combination of traits comprising a medium to dark greyish green color of the young fruit, a circular fruit shape in longitudinal section, a green ground color of the fruit skin with medium intensity and a yellowish hue, a small to medium size of the pistil scar, a reddish orange flesh color, and intermediate resistance to powdery mildew *Podosphaera xanthii* (Px) race 1, race 2, race 5.

24. A method of introducing a desired trait into a parent plant of hybrid melon variety 34-765 RZ comprising: (a) crossing a parent plant of hybrid melon variety 34-765 RZ, representative seed of which having been deposited under NCIMB Accession No. NCIMB 42128 with a second melon plant that comprises the desired trait to produce F1 progeny; (b) selecting an F1 progeny that comprises the desired trait; (c) crossing the selected F1 progeny with said parent plant of melon variety 34-765 RZ, to produce backcross progeny and (d) selecting backcross progeny comprising the desired trait and the physiological and morphological characteristics of said parent plant of melon variety 34-765 RZ, when grown in the same environmental conditions.

25. The method of claim 24 further comprising: (e) repeating steps (c) and (d) one or more times in succession to produce selected fourth or higher backcross progeny that comprise the desired trait and all of the physiological and morphological characteristics of said parent plant of melon variety 34-765 RZ, when grown in the same environmental conditions.

26. The method of claim 24 wherein the parent plant is obtained by reverse breeding.

27. A method of determining the genotype of a plant of melon variety 34-765 RZ, representative seed of which has been deposited under NCIMB Accession No. NCIMB 42128, or a first generation progeny thereof, comprising obtaining a sample of nucleic acids from said plant and comparing said nucleic acids to a sample of nucleic acids obtained from a reference plant, and detecting a plurality of polymorphisms between the two nucleic acid samples, wherein the plurality of polymorphisms are indicative of melon variety 34-765 RZ and/or give rise to the expression of any one or more, or all, of the morphological and physiological characteristics of melon variety 34-765 RZ as claimed in claim 1.

28. The method of claim 27 additionally comprising the step of storing the results of detecting the plurality of polymorphisms on a computer readable medium, or transmitting the results of detecting the plurality of polymorphisms.

29. The melon plant of claim 11 wherein said combination of traits further comprises fruits that are absent or very sparse in spot density, strong development of lobes of the leaf blade, a short to medium length of the peduncle of the fruit, and a large dark area around the peduncle of the young fruit.

30. A seed of the plant of claim 11.

31. A part of the plant of claim 11, wherein said plant part is suitable for sexual reproduction.

32. The plant part as claimed in claim 31, wherein said plant part comprises a microspore, pollen, an ovary, an ovule, an embryo sac or an egg cell.

33. A part of the plant of claim 11, wherein said plant part is suitable for vegetative reproduction.

34. The plant part as claimed in claim 33, said plant part comprises a cutting, a root, a stem, a cell or a protoplast.

35. A tissue culture of regenerable cells from the melon plant of claim 11.

36. The tissue culture as claimed in claim 35, wherein said cell or protoplast is derived from a leaf, pollen, an embryo, a cotyledon, a hypocotyl, a meristematic cell, a root, a root tip, an anther, a flower, a seed or a stem.

* * * * *